(12) United States Patent
Haywood

(10) Patent No.: US 9,370,391 B2
(45) Date of Patent: Jun. 21, 2016

(54) CATHETER, APPARATUS FOR CREATING A LINEAR ABLATION AND A METHOD OF ABLATING TISSUE

(75) Inventor: Guy Haywood, Plymouth (GB)

(73) Assignee: PLYMOUTH HOSPITALS NHS TRUST, Plymouth (GB)

( * ) Notice: Subject to any disclaimer, the term of this patent is extended or adjusted under 35 U.S.C. 154(b) by 928 days.

(21) Appl. No.: 11/658,819

(22) PCT Filed: Jul. 25, 2005

(86) PCT No.: PCT/GB2005/002895
§ 371 (c)(1),
(2), (4) Date: Jan. 26, 2007

(87) PCT Pub. No.: WO2006/010908
PCT Pub. Date: Feb. 2, 2006

(65) Prior Publication Data
US 2009/0005769 A1    Jan. 1, 2009

(30) Foreign Application Priority Data
Jul. 27, 2004   (GB) .................................. 0416713.6

(51) Int. Cl.
*A61B 18/14* (2006.01)
*A61B 18/02* (2006.01)
*A61B 18/00* (2006.01)

(52) U.S. Cl.
CPC ............. *A61B 18/02* (2013.01); *A61B 18/1492* (2013.01); *A61B 2018/00273* (2013.01); *A61B 2018/0212* (2013.01)

(58) Field of Classification Search
CPC .... A61B 18/02; A61B 18/0218; A61B 18/14; A61B 18/1492; A61B 2018/00005; A61B 2018/00273; A61B 2018/00351; A61B 2018/00577; A61B 2018/0212
USPC ........................ 606/20–26; 607/126; 600/375
See application file for complete search history.

(56) References Cited

U.S. PATENT DOCUMENTS

| | | | |
|---|---|---|---|
| 4,281,660 A * | 8/1981 | Fujiwara | ........................ 600/375 |
| 5,281,213 A | 1/1994 | Milder et al. | |
| 5,281,215 A | 1/1994 | Milder | |
| 5,423,804 A | 6/1995 | Kulick | |

(Continued)

FOREIGN PATENT DOCUMENTS

| | | |
|---|---|---|
| EP | 1129670 | 9/2001 |
| EP | 1430848 | 6/2004 |

(Continued)

OTHER PUBLICATIONS

ISR dated Nov. 7, 2005 for PCT/GB2005/002895 (in English).
Written Opinion for PCT/GB2005/002895 (in English).
British Search Report dated Oct. 28, 2004 for GB 0416713.6.

*Primary Examiner* — Michael Peffley
*Assistant Examiner* — Samantha Good
(74) *Attorney, Agent, or Firm* — Kilpatrick Townsend & Stockton LLP

(57) ABSTRACT

A catheter is provided with an anchoring member for anchoring a part of a linear ablating head of the catheter to a structure. The structure can be a cryogenically anchored point catheter. This allows the surgeon to position the linear catheter more exactly in the heart chamber and overcomes the adverse effects of the slippery and irregular heart chamber walls.

30 Claims, 5 Drawing Sheets

(56) References Cited

U.S. PATENT DOCUMENTS

| | | | |
|---|---|---|---|
| 5,487,385 A | 1/1996 | Avitall | |
| 6,217,584 B1* | 4/2001 | Nun | 606/107 |
| 6,595,989 B1 | 7/2003 | Schaer | |
| 2001/0035189 A1* | 11/2001 | Dobak, III | 128/898 |
| 2002/0062124 A1* | 5/2002 | Keane | 606/41 |
| 2003/0135207 A1 | 7/2003 | Langberg et al. | |
| 2003/0204187 A1 | 10/2003 | Hintringer et al. | |
| 2004/0034347 A1 | 2/2004 | Hall et al. | |
| 2004/0204705 A1* | 10/2004 | Lafontaine | 606/21 |

FOREIGN PATENT DOCUMENTS

| | | |
|---|---|---|
| WO | 95/19738 | 7/1995 |
| WO | 98/37822 | 9/1998 |
| WO | 99/52455 | 10/1999 |
| WO | 00/32126 | 6/2000 |
| WO | 00/42933 | 7/2000 |
| WO | 00/67832 | 11/2000 |

* cited by examiner

CATHETER, APPARATUS FOR CREATING A LINEAR ABLATION AND A METHOD OF ABLATING TISSUE

CROSS-REFERENCE TO RELATED APPLICATIONS

This application is a 371 US National Stage of International Application No. PCT/GB2005/002895, filed Jul. 25, 2005. This application claims the benefit of GB Patent Application 0416713.6, filed Jul. 27, 2004. The disclosure of the above applications is incorporated herein by reference.

FIELD OF THE INVENTION

The present invention relates to catheters, apparatus comprising catheters and methods of using catheters. The invention more particularly can be applied to a catheter system used for tissue ablation in the heart.

BACKGROUND OF THE INVENTION

Many medical procedures are performed using minimally invasive surgical techniques, wherein one or more slender implements are inserted through one or more small incisions into a patient's body. With respect to ablation, the surgical implement can include a rigid or flexible structure having an ablation device at or near its distal end that is placed adjacent to the tissue to be ablated. Radio frequency energy, microwave energy, laser energy, extreme heat, and extreme cold can be provided by the ablation device to electrically inactivate the tissue.

With respect to cardiac procedures, a cardiac arrhythmia such as atrial fibrillation or a focal atrial tachycardia can be treated through-selective ablation of cardiac tissue to eliminate or isolate the source of the arrhythmia. A popular minimally invasive procedure, radio frequency (RF) catheter ablation, frequently includes a preliminary step of electrocardiographic mapping followed by the creation of one or more ablated regions (lesions) in the cardiac tissue using, RF energy. In the case of atrial fibrillation ablation, multiple lesions are required to obtain a successful result. Often five, and sometimes as many as sixty, lesions may be required before a successful result is attained.

Deficiencies of radio frequency ablation devices and techniques have been overcome by using cold to do zero degree or ice mapping (at −20° C. for example) prior to creating lesions, as taught in U.S. Pat. Nos. 5,423,807; 5,281,213; and 5,281,215. However, even though combined cryogenic mapping and ablation devices permit greater certainty and less tissue damage than RF devices and techniques both the cryogenic and the RF devices are configured for spot or roughly circular tissue ablation.

Spot tissue ablation is acceptable for certain procedures. However, other procedures can be more therapeutically effective if multiple spot lesions along a predetermined line, or a single elongate or linear lesion is created in a single ablative step. Radio frequency ablation devices are known to be able to create linear lesions by dragging the ablation tip along a line while it is active.

WO 00/32126, WO 98/37822 and EP 1,129,670 each disclose catheters suitable for linear ablation. However, these catheters present practical difficulties to the surgeon in use. More specifically, the inner wall chambers of the heart, such as the atrial wall, are irregular and slippery and the surgeon encounters a problem in stably positioning the linear catheter in the desired location with sufficient contact at the catheter/tissue surface for the required amount of time to create an effective unbroken line of ablation.

A catheter designed to be more suitable for ablation of an irregular surface is disclosed in WO 99/52455. However, this catheter still suffers the problem that it is difficult to position it stably and accurately due to the deformable nature of the tissue walls.

U.S. Pat. No. 6,595,989, US 2003/0204187 and US 2004/0034347 all suggest using an inflatable balloon to anchor a structure in a cardiac vessel orifice, such as the pulmonary vein. Such devices have the drawback that the structure can be anchored only in a select few positions where veins exist. It can be very difficult for the surgeon to create selective ablations at positions far away from the anchoring point in the vein, for example.

It would be beneficial if there existed apparatus that made it possible to push a linear ablating device against tissue walls (e.g. the wall of the heart muscle) so as to ensure good contact at all points along the whole active length of the linear ablating device without the device slipping out of position. It would also be desirable if there existed apparatus that gave the surgeon a high degree of freedom in positioning the linear ablating device such that a selected ablation can be performed easily and quickly at any point on the tissue that the surgeon chooses.

BRIEF SUMMARY OF THE INVENTION

The present invention provides a catheter for creating a linear ablation on tissue, the catheter having an anchoring member that assists in stably positioning the catheter with respect to the tissue.

In an exemplary embodiment there is provided apparatus constructed and arranged to create a linear ablation on tissue, said apparatus comprising: a cryogenic catheter capable of being stably positioned with respect to tissue via the formation of an ice ball; and a linear ablating section for creating said linear ablation; said linear ablating section being anchored, in use, to said cryogenic catheter.

The cryogenic catheter is a blunt-tipped catheter and is desirably actuatable separately from the linear ablating section. The linear ablating section is preferably a section of a linear catheter. The linear ablating section may comprise a section delivering radio frequency energy, cryo-cooling, microwave energy, ultrasound, laser energy or any other agent capable of resulting in electrical inactivation of the tissue.

The linear ablating section is conveniently anchored to the cryogenic catheter by an anchoring member.

The anchoring member is preferably associated with a distal end of the linear ablating section and can conveniently consist of a wire loop. The wire loop is used to anchor part of the linear ablating section of the linear catheter to a structure, such as an already stably positioned point catheter.

The wire loop is preferably adjustable by remote control using one or more loop control wires so as to allow it to be increased and decreased in diameter. This allows the wire loop to be stably anchored to the cryogenic catheter (by tightening the loop) or to be movable with respect to the cryogenic catheter (by loosening the loop). In order to prevent the wire loop being locked tight, a diameter restrictor that sets a minimum possible diameter for the wire loop can be provided.

The linear catheter may comprise a cryogenic ablating head and a cryogenic fluid circuit can be utilised in this case.

Other types of ablation head e.g. those utilising radio frequency energy, microwave energy, laser energy or extreme heat can also be used.

The present invention also provides a method of ablating tissue, said method comprising: anchoring a linear ablating catheter to said cryogenic catheter; stably positioning a cryogenic catheter to said tissue via the formation of an ice ball; positioning the rest of the linear ablating catheter to form a linear ablation region on said tissue; and ablating the tissue to form a linear ablation along said linear ablation region.

The method is particularly applicable to the internal surface tissue of a heart chamber, such as the left atrium. The anchoring member of the present invention can take any form and may, for example, comprise a wire loop or pivot member.

BRIEF DESCRIPTION OF THE DRAWINGS

The present invention will now be further described, by way of non-limitative example only, with reference to the accompanying schematic drawings, in which:—

DETAILED DESCRIPTION OF THE INVENTION

Figure 1:
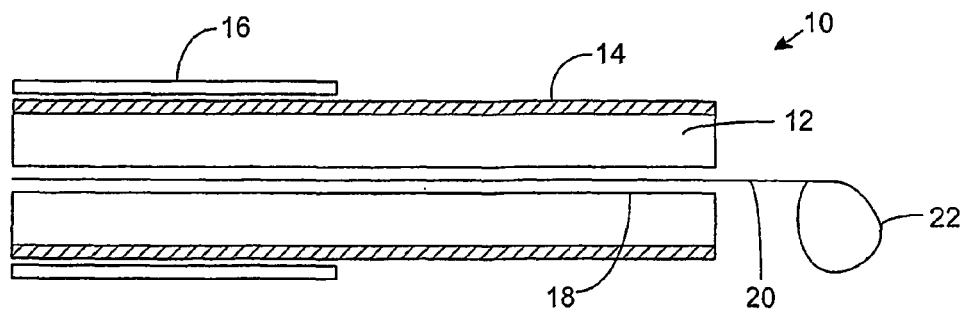
FIG. 1 shows a longitudinal cross-section view of the distal end of a linear ablation catheter according to a first embodiment of the invention.
Figure 5:
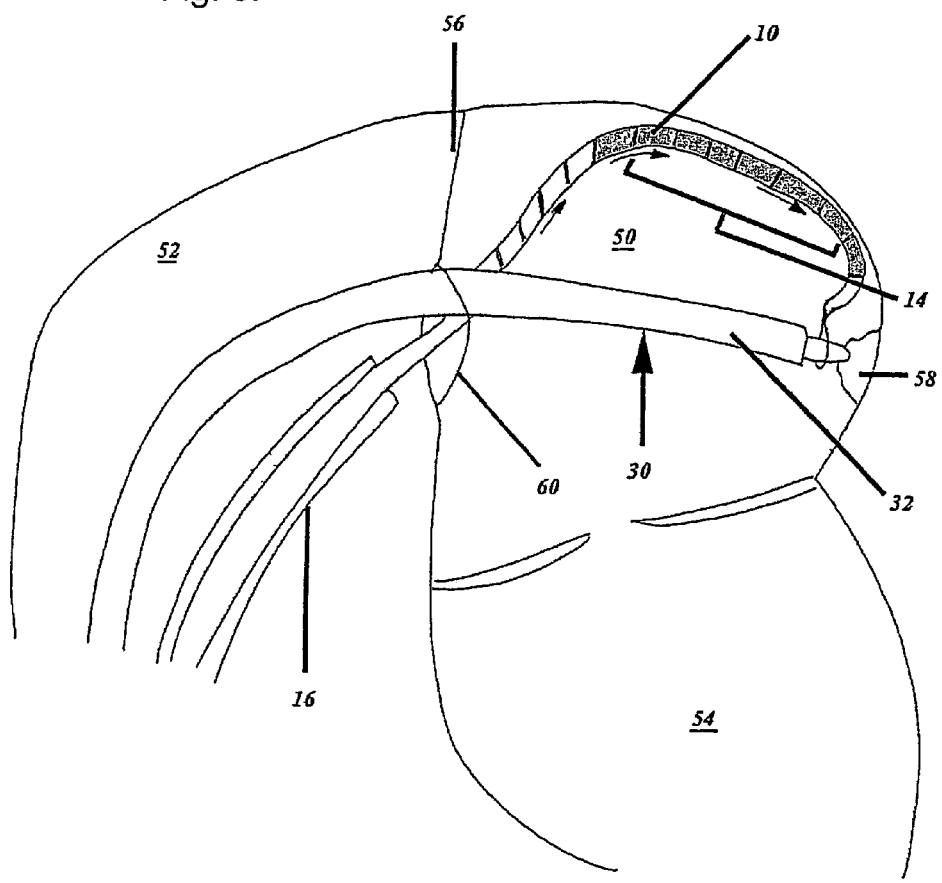
FIG. 5 is similar to Fig. 4, but shows the linear catheter stably positioned against the tissue.

FIG. 1 is a schematic illustration of a cryosurgical linear catheter 10 in accordance with one aspect of the invention. A cryogenic catheter with a wire loop is discussed merely for the purposes of illustration and other types of linear catheter can be used in practice, with other types of anchoring member, as discussed below. Only the distal part of the catheter is shown in FIG. 1. The catheter comprises a flexible member 12 having a thermally transmissive region 14 and a fluid path (not shown) through the flexible member to the thermally transmissive region. The fluid path is provided between the thermally transmissive region to a point external to the catheter, such as its proximal end (not shown). The thermally transmissive region is the linear ablation section of the catheter which, when in contact with the tissue, causes ablation of that tissue. The thermally transmissive region does not usually extend the whole length of the catheter and is preferably confined to a portion of the catheter near or at its distal end. For example, FIG. 5 shows a linear catheter in which the thermally transmissive region 14 is shown shaded.

The fluid paths allow a cryogenic fluid (e.g. nitrous oxide, liquid oxygen) to be brought from a point external to the catheter to the thermally transmissive region and to be returned to an external point, in a circuit. The fluid accepts the heat drawn from the tissue in use, so as to cool the tissue.

In exemplary embodiments of the invention, the thermally transmissive region 14 of the catheter is deformable. One type of deformation is from a linear configuration to an arcuate configuration and this may be accomplished using mechanical and/or electrical devices known to those skilled in the art. For example, a wall portion of the flexible member 12 can include a metal braid to make the catheter torqueable for overall catheter steering and placement. Additionally or alternatively, a cord, wire or cable can be incorporated with, or inserted into, the catheter for deformation of the thermally transmissive region 14.

A support sheath 16 is provided around the flexible member 12 and may be retractable therefrom. In the preferred embodiment, the flexible member 12 is retractable so as to be completely envelopable by the support sheath 16 if necessary. This assists in inserting and removing the catheter from the patient's body.

The linear catheter preferably comprises an anchoring member that can be used to anchor some part of the linear catheter to a structure. Such anchoring assists in stably positioning the linear catheter whilst creating ablations. The anchoring member can, for example, be a member that is used to attach a part of the linear catheter to another catheter, such as a point catheter. A preferable construction of anchoring member is a wire loop which is used to snare a point catheter so as to stably position a part of the linear catheter with respect to the point catheter. Such a construction is described below.

Referring to FIG. 1, a guide passageway 18 is provided longitudinally along the centre of the linear catheter and in this passageway is provided a loop control wire 20 having at its distal end a wire loop 22. The wire loop 22 is preferably configured in the form a noose such that tension on the control wire 20 causes the wire loop 22 to tighten when it is positioned around a suitable structure. Such tightening is preferably elastic in nature such that removal of the tension on the control wire 20 allows the wire loop 22 to open again. In this way, the diameter of the wire loop 22 may be established by remote control. Although this is not shown in FIG. 1, a loop diameter restrictor may be utilized which prevents the loop diameter from falling below a given predetermined value. The loop diameter restrictor can be a physical obstruction on the wire of the loop 22.

Figure 2:
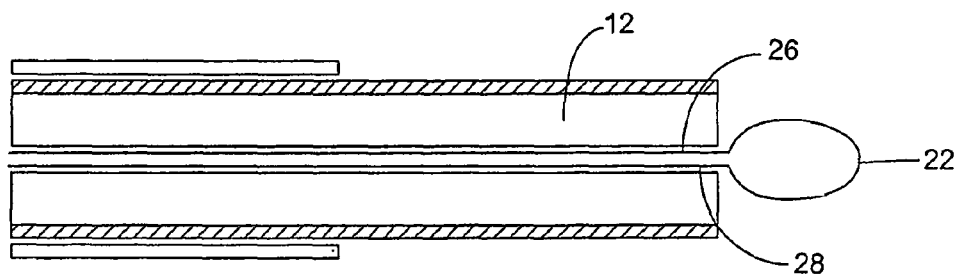
FIG. 2 shows a longitudinal cross-section view of the distal end of a linear ablation catheter according to a second embodiment of the invention with the wire loop extended.
Figure 3:
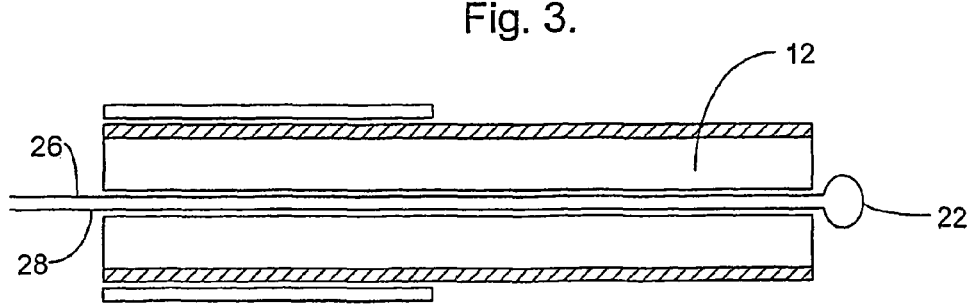
FIG. 3 shows a longitudinal cross-section view of the distal end of the linear ablation catheter according to the second embodiment of the invention with the wire loop retracted.

FIGS. 2 and 3 show an alternative embodiment in which the wire loop 22 has a pair of control wires 26, 28. FIG. 2 shows the position when the wire loop is extended and FIG. 3 shows the position when the wire loop 22 is retracted somewhat. Control of the size of wire loop 22 is achieved by applying tension to one or both of the control wires 26, 28. Applying a tension such that the wires retract into the flexible member 12 causes the size of wire loop 22 to diminish. The wire loop can be opened again by pushing one or both of control wires 26, 28 along flexible member 12. One of the control wires 26, 28 can be dispensed with if the wire loop 22 is attached to the distal end of the catheter 10. For example, loop 22 can be attached to the distal end of the catheter instead of control wire 26 and the loop diameter can be set using control wire 28 only.

The flexible member 12 may take any of the forms shown in WO 00/32126 and the cryogenic cooling path can be arranged in any of the configurations disclosed in that document. Some slight modification may be required to accommodate the guide passageway 18, which will be apparent to those skilled in the art.

The invention is also intended to cover linear catheters that use other means to perform the ablation, for example radio frequency (RF) energy. When a radio frequency energy linear catheter is used, for example, the thermally transmissive region 14 shown in FIGS. 1 to 3 is replaced by a linear ablating section that transmits radio frequency energy. Such radio frequency energy serves to create ablations on tissue. Linear catheters using other technologies such as microwave energy, ultrasound, laser or any other agent capable of providing an electrical inactivation or "ablation" of the tissue can be used. In these embodiments, the linear ablating sections of the linear catheter are conventional.

Any of the anchoring members disclosed herein can be used with any of these linear catheters. For example, the wire loop configuration shown in FIGS. 1 to 3 can equally be applied to radio frequency linear catheters as to cryogenic linear catheters.

Instead of going through the centre of the catheter 10, the guide passageway 18 can be routed along one side thereof. When a cryogenic linear catheter is used, this removes the need to modify the cryogenic fluid paths shown in WO 00/32126.

The configuration shown in FIGS. 1 to 3 with a wire loop 22 extending out of the distal end of the catheter 10 is merely a preferred configuration. Any configuration of anchoring member which allows the catheter to be more stably positioned is intended to be encompassed. For example, the wire loop 22 could extend from one side wall of the catheter 10 near the distal end, or, could extend from a point some distance from the distal end. It is preferable, however, that the anchoring member 22 is associated with the distal end of the linear catheter. This simplifies the maneuvers required by the surgeon in positioning the catheter.

Figure 4:
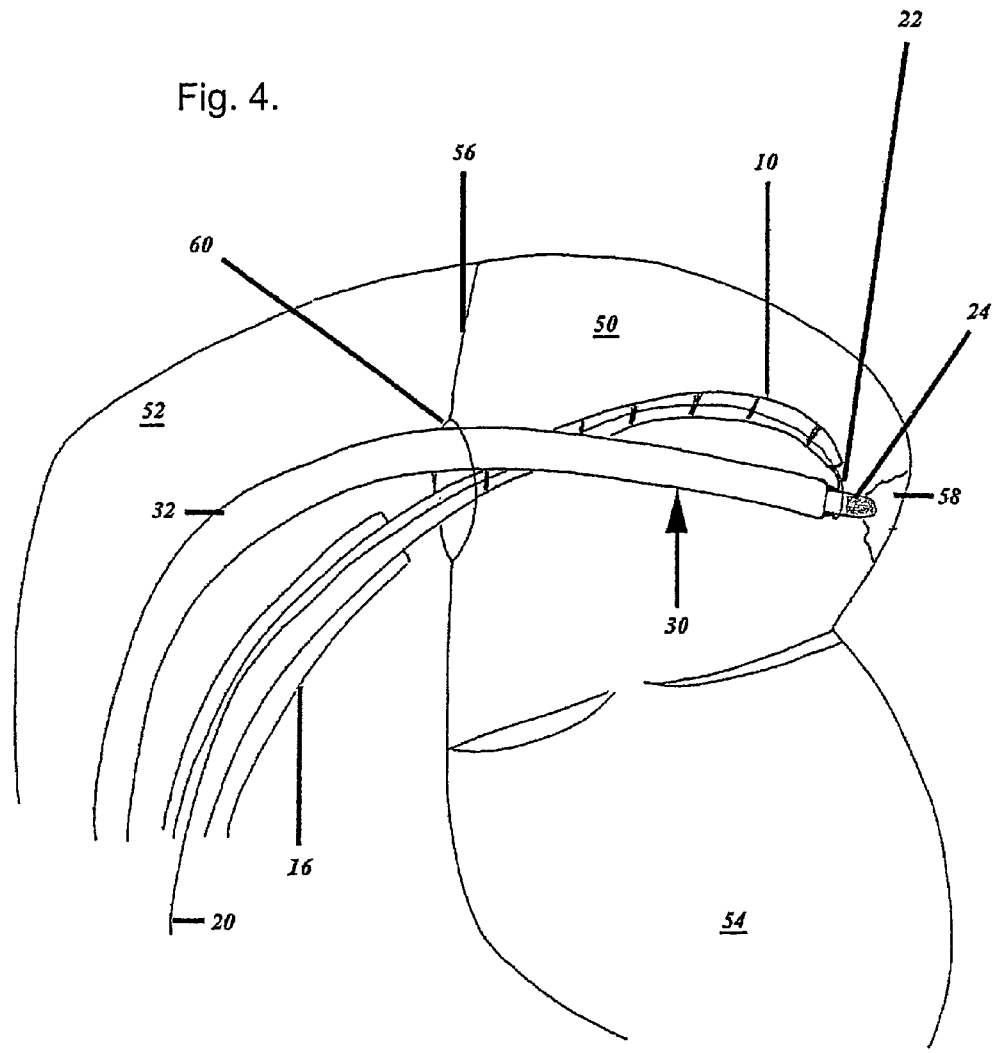
FIG. 4 shows two catheters introduced into the left atrium of a heart in accordance with the present invention.

A preferred use of the catheter shown in FIG. 1 will now be described with reference to FIGS. 4 and 5. These Figures schematically show a heart having a left atrium 50, a right atrium 52 arid a left ventricle 54. In the method, the septum 56 separating the left and right atria is punctured and the catheter 10 of FIG. 1 and a conventional point catheter 30 are commonly fed through this transeptal puncture 60. The point catheter 30 has a blunt point-shaped thermally transmissive region 24. As used herein, the terms "point catheter" and "point-shaped" are used to distinguish the smaller thermally transmissive region 24 of the "point" catheter 30 from the longer thermally transmissive region 14 of the linear catheter 10. The point catheter is maneuvered by the surgeon through the wire loop 22 of the linear catheter to a position adjacent the left atrium wall, as is seen in FIG. 4. As the point catheter is blunt, it does not penetrate the heart tissue during this step. The point catheter is then activated so as to freeze itself onto a point of the left atrium wall. In this freezing process an ice ball 58 is formed between the blunt tip of the point catheter and the heart tissue. The ice ball 58 at the catheter/tissue interface acts to provide a stable anchoring point. The configuration at this time is shown in FIG. 4.

The wire loop 22 is then tightened by applying tension to the loop control wire 20 so as to stably anchor the linear catheter 10 to the point catheter 30. The linear catheter 10 is then advanced out of its support sheath 16 so that the catheter bows out against the left atria wall ensuring good contact between the catheter and the atrium. The tissue is quite deformable and the pushing of the catheter helps to deform the irregular tissue shape into an arc shape, allowing good contact along the active length of the catheter. This is shown in FIG. 5.

The cryogenic fluid is then be flowed through the fluid paths of the catheter so as to rapidly cool the thermally transmissive region 14 of the linear catheter 10. This cools the adjacent tissue and ablates it to form an unbroken linear lesion along the linear ablation region. The linear ablation serves to block electrical signals, preventing the arrhythmia. When other ablation modalities are used (e.g. radio frequency energy, microwave energy, etc.), cryogenic fluid is not used and instead the necessary procedure is carried out in accordance with the ablation modality (e.g. a linear radio frequency head is activated in the case of radio frequency ablation).

Once the linear ablation has been completed, the flow of cryogenic fluid can be stopped and the linear catheter 10 can be advanced back into its sheath 16 somewhat to remove it from contact with the tissue wall. The linear catheter can then be repositioned (for example by rotating it) about the same anchor point so as to create a further linear ablation. In this manner, a series of radial linear ablations stemming from the anchoring point can be created. If overlapping ablations are required, the point catheter 30 can be repositioned to allow a further series of ablations having a different anchoring point to be created.

The point catheter 30 is provided with a retractable sheath 32. Preferably, the outside diameter of the retractable sheath 32 is larger than the minimum diameter of the wire loop 22. This ensures that the wire loop 22 will not slip down the point catheter 30 past the sheath 32 when the wire loop 22 is tightened. Furthermore, it allows the point catheter 30 to be retracted somewhat into its sheath 32 so as to hold the wire loop 22 in place against the ice ball 58. This creates a very stable anchoring for the distal point of the linear catheter 10.

The point catheter is usefully made less flexible or virtually rigid at its distal end, for example over the end 5 to 7 cm. This helps to achieve a stable position and provide a stable anchoring point for the linear ablation catheter.

In the above described method, the septum 56 is punctured to allow access of the catheters. However, any useful access of the catheters is envisaged including retrograde access via the femoral artery with the catheters retrogradely crossing the aortic and mitral valves to access the left atrium.

Figure 6:
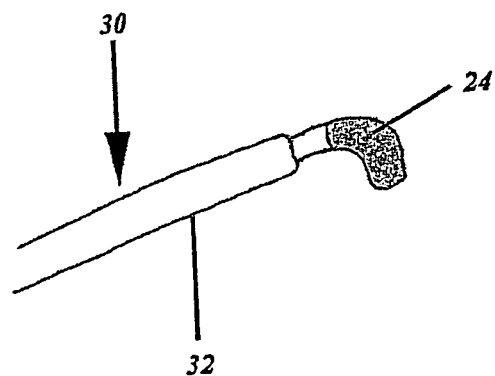
FIG. 6 shows an alternative tip design for the point catheter used in the present invention.

FIG. 6 shows an alternative configuration for the tip of the point catheter 30. In this configuration, rather than having a conventional point tip, the catheter 30 has a curved tip 24 shaped like the end of a hockey stick. This shape presents a greater surface area to the inner tissue of the atrium wall allowing better cryo-anchoring.

Preferably, the tip 24 is flexible enough to allow it to straighten out so that it can be fully retracted into the sheath 32.

Figure 7:
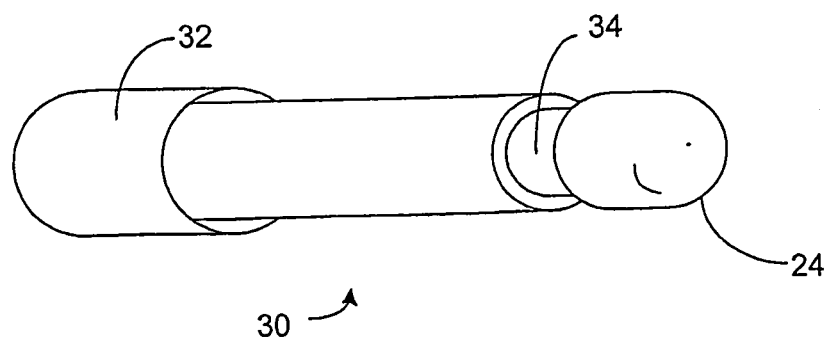
FIG. 7 shows another design for the tip of a point catheter of the present invention.

FIG. 7 shows an alternative tip profile for the point catheter. As shown in FIG. 7, there is a recessed portion 34 near to the tip 24 of the point catheter 30. This recessed portion allows the linear catheter 10 to be better attached to the point catheter 30. For example, the wire loop 22 is, in use, placed over the tip 24 and is slid down the point catheter 30 until it is at the location of the recess 34. The wire loop 22 is then tightened around the reduced diameter section of the recess 34. The configuration means that the wire loop can thereafter no longer slide very far longitudinally along the point catheter 30.

In a preferable embodiment, the recess 34 is located close to the tip 24 such that when ice ball 58 is produced, the connection between the linear catheter and the point catheter is encapsulated in the ice ball.

It is possible to use this recessed configuration in any of the embodiments of point catheters disclosed herein. In particular, the recess 34 can be used in combination with the hockey stick shaped catheter of FIG. 6.

Figure 8A:
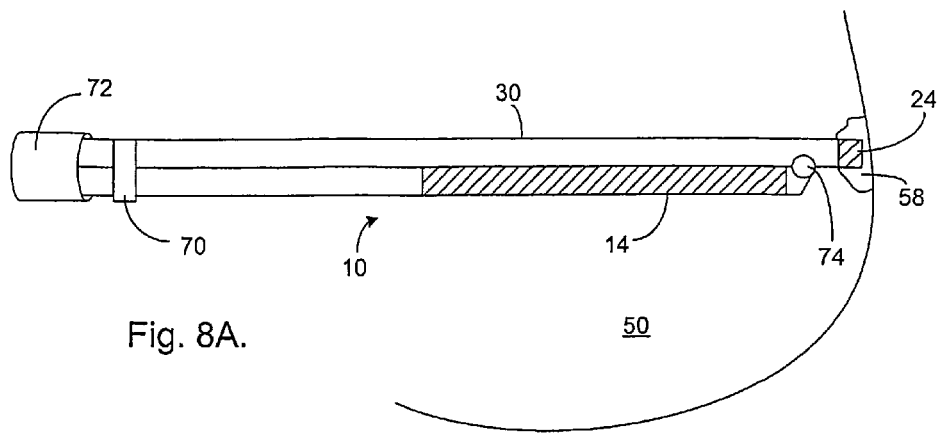
FIGS. 8A to 8C show three stages in the placement of apparatus according to another embodiment of the invention.
Figure 8B:
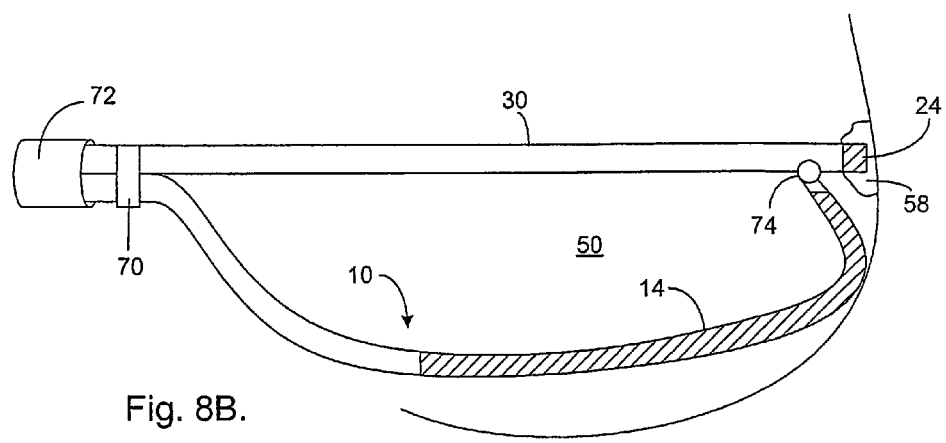
Figure 8C:
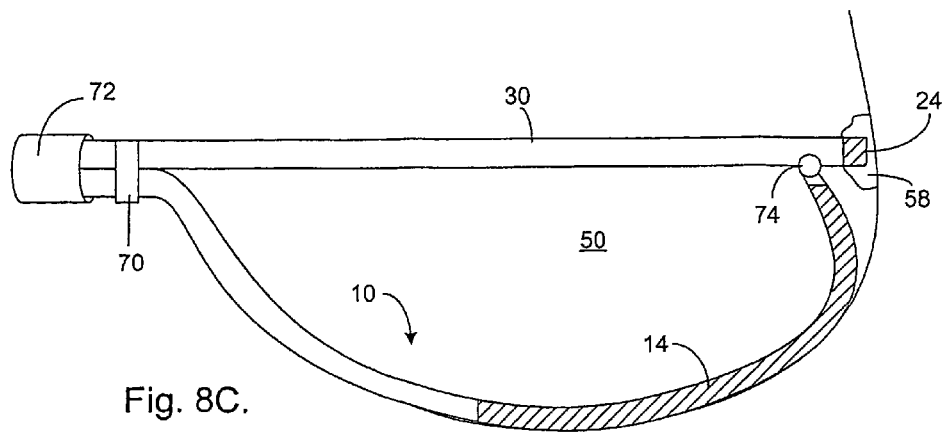

FIGS. 8A, 8B and 8C show a further embodiment of the invention. In this embodiment, the point catheter 30 and linear catheter 10 are provided together in a common sheath 72. A guide bracket 70 is attached to the point catheter 30 and acts to guide the linear catheter 10 which can be moved longitudinally along the point catheter 30 at the position of the guide bracket 70. The linear catheter 10 is permanently attached at its distal end by anchoring member 74 to the point catheter 30. The anchoring member 74 is shown here as being a pivot but any anchoring member can be used in practice, such as a wire loop as disclosed above. The linear ablating section 14 is also shown in FIGS. 8A, 8B and 8C.

During use of this embodiment, the entire structure is advanced out of its sheath 72 such that the point 24 of the point catheter 30 is adjacent to an area of tissue forming the wall of the chamber 50. The point catheter is then activated so as to create ice ball 58 which stably positions point catheter 30 in the chamber 50. The linear catheter 10 can then be fed forward along the sheath 72 such that it is guided by bracket 70 and bows out away from point catheter 30, as shown in FIG. 8B. Continued feeding of linear catheter 10 causes the linear ablating section 14 to bow out against the wall of chamber 50 so as to provide an unbroken line of contact. The linear catheter is then activated so as to create a linear ablation on the chamber wall. Multiple ablations can be performed in the manner described with reference to FIGS. 4 and 5.

Once the necessary ablations have been made, the linear catheter 10 can be pulled back along the sheath 72 such that it returns to the position shown in FIG. 8A. The entire device can then be retracted into sheath 72 and removed from the body.

The apparatus and method of the present invention represents an improvement over the prior art techniques for correcting heart arrhythmia such as atrial fibrillation. The invention makes it easier for the surgeon to achieve long lines of linear scar tissue on the wall of the atrium in order to create the lines of electrical block which prevent the swirling circuits that drive the arrhythmia from turning freely in the atrial chamber walls. The invention allows good contact along the length of the linear ablation catheter and reduces the adverse effects of the irregular and slippery atrial wall.

The invention claimed is:

1. An apparatus, comprising:
    a cryogenic catheter comprising a blunt thermally transmissive tip, said cryogenic catheter being configured to form an ice ball between said blunt tip and a first section of heart tissue to thereby stably affix said cryogenic catheter to said first section of heart tissue without said tip penetrating any heart tissue; and
    a continuous elongated linear ablating section that extends in a longitudinal direction to present an elongated longitudinally-extending surface, said continuous elongated linear ablating section being spaced apart from said blunt tip and being configured for creating a continuous elongated linear ablation along a second section of heart tissue by pressing the elongated longitudinally-extending surface of said continuous elongated linear ablating section against the second section of heart tissue without said continuous elongated linear ablating section penetrating any heart tissue,
    wherein said second section of heart tissue is spaced apart from said first section of heart tissue such that a third section of heart tissue, disposed between said first and second sections of heart tissue, is unablated and does not have the ice ball disposed thereon,
    wherein said continuous elongated linear ablating section is anchored, in use, to said cryogenic catheter.

2. The apparatus according to claim 1, wherein said cryogenic catheter is actuatable separately from said linear ablating section.

3. The apparatus according to claim 1, wherein said linear ablating section is anchored to said cryogenic catheter by an anchoring member.

4. The apparatus according to claim 3, wherein said anchoring member is attached to a distal end of said linear ablating section.

5. The apparatus according to claim 4, wherein said anchoring member is a pivoted attachment point.

6. The apparatus according to claim 3, wherein said anchoring member comprises a wire loop.

7. The apparatus according to claim 6, wherein said wire loop is adjustable by remote control using a loop control wire.

8. The apparatus s according to claim 7, wherein said control wire is routed through a guide passageway along the length of said linear ablating section.

9. The apparatus according to claim 8, wherein said guide passageway is along the center of said linear ablating section.

10. The apparatus according to claim 8, wherein said guide passageway is along the outside of said linear ablating section.

11. The apparatus according to claim 6, wherein said wire loop comprises a loop diameter restrictor that sets a minimum possible diameter for said wire loop.

12. The apparatus according to claim 1, further comprising a sheath surrounding said linear ablating section and being retractable therefrom.

13. The apparatus according to claim 12, further comprising an additional sheath around said cryogenic catheter.

14. The apparatus according to claim 12, wherein the sheath is further disposed around said cryogenic catheter.

15. The apparatus according to claim 12, wherein said linear ablating section is anchored to said cryogenic catheter by an anchoring member comprising a wire loop, and wherein said sheath has an outer diameter that is greater than a minimum diameter of the wire loop, so as to prevent said wire loop from slipping down said cryogenic catheter.

16. The apparatus according to claim 1, wherein said linear ablating section comprises an elongated cryogenic ablating head for ablating the second section of heart tissue by reducing the temperature of said second section of heart tissue.

17. The apparatus according to claim 16, further comprising a cryogenic fluid circuit for circulating cryogenic fluid through the elongated cryogenic ablating head in order to carry out cryogenic ablation.

18. The apparatus according to claim 1, wherein said linear ablating section comprises an elongated radio frequency linear ablating head.

19. The apparatus according to claim 1, wherein said linear ablating section is steerable by remote control using a steering control wire.

20. The apparatus according to claim 1, wherein said cryogenic catheter defines an axial direction and wherein said tip comprises a transverse component at a distal end of the tip, wherein the transverse component has a longitudinal direction that is generally transverse to the axial direction of the cryogenic catheter.

21. The apparatus according to claim 1, wherein said linear ablating section is part of a linear ablation catheter.

22. The apparatus according to claim 21, wherein said cryogenic catheter comprises a guide bracket for supporting said linear ablation catheter and for allowing said linear ablation catheter to advance therealong.

23. A method of ablating heart tissue using a blunt cryogenic tip connected to a linear ablating section, said method comprising:
    positioning said blunt cryogenic tip adjacent a section of said heart tissue without penetrating any heart tissue;

activating said blunt cryogenic tip to thereby form an ice ball between said blunt cryogenic tip and said section of heart tissue, whereby the ice ball stably affixes said blunt cryogenic tip to said section of heart tissue;

positioning an elongated longitudinally-extending surface of said linear ablating section so as to be adjacent a continuous elongated linear ablation region on said heart tissue without penetrating any heart tissue; and activating said linear ablating section such that said elongated longitudinally-extending surface of said linear ablating section ablates said continuous elongated linear ablation region to create a continuous linear ablation spaced apart from said section of heart tissue, wherein said continuous linear ablation region is spaced apart from said section of heart tissue such that an additional section of heart tissue, disposed between said continuous linear ablation region and said section of heart tissue, is unablated and does not have the ice ball disposed thereon.

24. The method according to claim 23, wherein said section of the heart tissue and said linear ablation region are internal surface tissue of a heart chamber.

25. The method according to claim 24, wherein said heart chamber is a left atrium.

26. The method according to claim 23, further comprising anchoring said linear ablating section to a cryogenic catheter comprising said cryogenic tip.

27. The method according to claim 26, wherein said anchoring of said linear ablating section to said cryogenic catheter comprises feeding said cryogenic catheter through a wire loop attached to said linear ablating section.

28. The method according to claim 26, wherein said anchoring of said linear ablating section to said cryogenic catheter comprises anchoring at an anchor point and said positioning of said linear ablating section comprises rotating said linear ablating section about said anchor point and longitudinally pushing said linear ablating section.

29. An apparatus, comprising:

a linear ablating head;

a blunt thermally transmissive cryogenic tip connected to said linear ablating head and spaced apart from said linear ablating head, said blunt tip being configured to form an ice ball between said tip and a first section of heart tissue to thereby stably affix said tip to said first section of heart tissue without said tip penetrating any heart tissue, said linear ablating head being connected to said blunt tip so that an elongated longitudinally-extending surface of the linear ablating head can be positioned to form a continuous elongated linear ablation on a second section of heart tissue without penetrating any heart tissue, said second section of heart tissue being spaced apart from said first section of heart tissue such that a third section of heart tissue, disposed between said first and second sections of heart tissue, is unablated and does not have the ice ball disposed thereon.

30. The apparatus according to claim 29, further comprising an anchoring member associated with said linear ablating head for anchoring a part of said linear ablating head to a cryogenic point catheter comprising said tip.

* * * * *